United States Patent [19]
Johnson et al.

[11] Patent Number: 5,456,257
[45] Date of Patent: Oct. 10, 1995

[54] ULTRASONIC DETECTION OF CONTRAST AGENTS

[75] Inventors: Keith W. Johnson, Lynnwood; Jeffry E. Powers, Lake Stevens, both of Wash.

[73] Assignee: Advanced Technology Laboratories, Inc., Bothell, Wash.

[21] Appl. No.: 344,266

[22] Filed: Nov. 23, 1994

[51] Int. Cl.⁶ .................................................. A61B 8/00
[52] U.S. Cl. ............................................. 128/662.02
[58] Field of Search ................ 128/662.02, 660.01; 424/9

[56] References Cited

U.S. PATENT DOCUMENTS

| | | | |
|---|---|---|---|
| 5,040,537 | 8/1991 | Katakura | 128/662.02 X |
| 5,135,000 | 8/1992 | Akselrod et al. | 128/662.02 |
| 5,255,683 | 10/1993 | Monaghan | 128/662.02 |
| 5,302,372 | 4/1994 | Lin et al. | 128/662.02 X |

Primary Examiner—Francis Jaworski
Attorney, Agent, or Firm—W. Brinton Yorks, Jr.

[57] ABSTRACT

An ultrasonic diagnostic system is provided which detects the presence of coated microbubble contrast agents in the body of a patient by transmitting ultrasonic energy which causes the destruction of the coated microbubbles and detects the microbubble destruction through phase insensitive detection and differentiation of echoes received from two consecutive ultrasonic transmissions. The destruction of a microbubble can also be used as a point source of acoustic energy for aberration correction, whereby the timing of the beamformer is adjusted from an analysis of beamformer signals resulting from a detected microbubble destruction event.

18 Claims, 3 Drawing Sheets

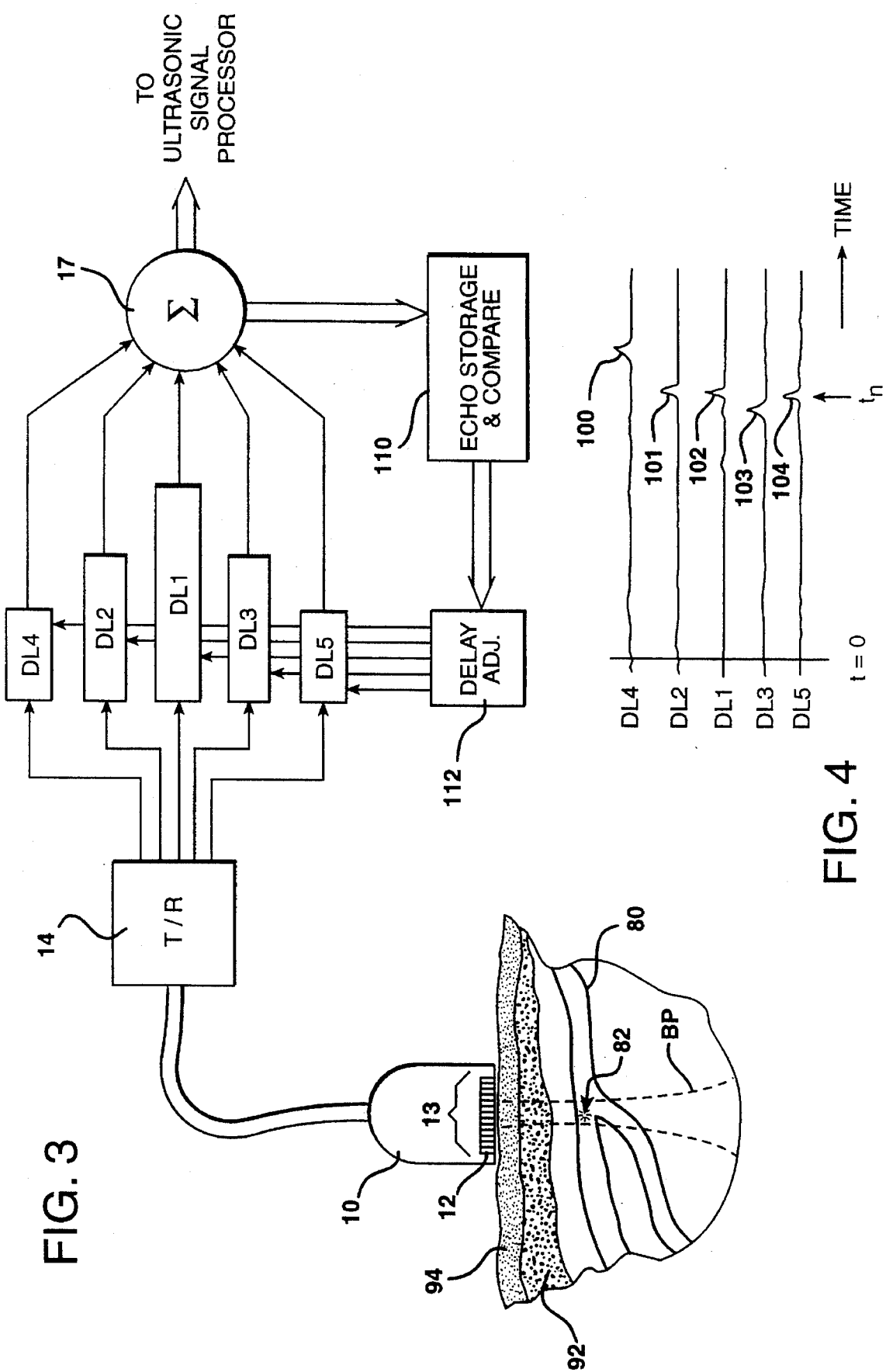

ULTRASONIC DETECTION OF CONTRAST AGENTS

This invention relates to improvements in the detection of ultrasonic contrast agents by ultrasonic diagnostic systems, and in particular to the detection and utilization of ultrasonic signals resulting from the use of contrast agents comprising coated microbubbles.

Ultrasonic diagnostic imaging system are capable of imaging and measuring the physiology within the body in a completely noninvasive manner. Ultrasonic waves are transmitted into the body from the surface of the skin and are reflected from tissue and cells within the body. The reflected echoes are received by the ultrasonic transducer and processed to produce an image or measurement of blood flow. Diagnosis is thereby possible with no intervention into the body of the patient.

However materials known as contrast agents can be introduced into the body to enhance ultrasonic diagnosis. Contrast agents are substances which will strongly interact with ultrasonic waves, such as by reflecting an increased amount of a transmitted ultrasonic wave as an echo. One substance which has been found to be especially useful as an ultrasonic contrast agent is air, in the form of tiny bubbles called microbubbles. Air bubbles are strong reflectors of ultrasonic energy due to the impedance mismatch of air and the material in which the bubbles are suspended. In order to infuse air into the body in a manner which will not harm the patient, and in a form in which the air will travel through the body and be expelled naturally, air has been suspended in solutions in the form of tiny microbubbles. Microbubble contrast agents are useful for imaging the body's vascular system, for instance, as the contrast agent can be injected into the bloodstream and will pass through the veins and arteries of the body with the blood supply until filtered from the blood stream in the kidneys and liver.

One type of microbubble contrast agent currently under investigation comprises coated microbubbles. The microbubbles of the contrast agent are covered with a thin biodegradable polymer coating or shell. The microbubbles have diameters between 0.1 and 4.0 μm and a specific density about $\frac{1}{10}$ of the density of water. The coated microbubbles are suspended in an aqueous solution for infusion into the blood stream.

Coated microbubbles have the advantage of being stable in the body for a significant period of time, as the polymeric shell serves to preserve the microbubble. The size of the microbubbles is chosen to provide the property of resonance of the coated microbubbles when insonified with energy at ultrasonic frequencies. The resonance of the microbubbles is relatively easy to detect through ultrasonic Doppler interrogation.

At moderately high sound pressure amplitudes the response of the microbubbles to ultrasonic energy can further become nonlinear, causing the shells to rupture. This acoustically induced destruction and collapse of the microbubbles produces a high amplitude B-mode response and a strong Doppler response and a characteristically bright pattern in the color Doppler mode. Hence color Doppler is becoming the preferred modality for detecting the collapse of the hollow spheres of coated microbubble contrast agents.

The collapse of the coated microbubbles in response to an ultrasonic pulse is a sudden, almost instantaneous event, however. The echo response from the destruction of the microbubble shell will only be present following the single Doppler wave that causes the shell to collapse. In color Doppler interrogation, which is done by interrogating the patient with a series of ultrasonic pulses called an ensemble, the result of the microbubble rupture will be present during an Doppler interrogation period. The present inventors have noticed that while color Doppler can effectively detect these events, these transient responses can be confusingly similar to the response engendered by tissue moving inside the body, or motion by the ultrasonic probe itself. These conditions can create undesirable Doppler artifacts called flash, so named for the sudden flash of Doppler color produced by the probe or tissue motion. Flash artifacts are generally removed from Doppler signals prior to color flow processing, and this removal can also eliminate the signals received from collapsing bubbles. It would be desirable to be able to detect the result of a microbubble rupture in a manner by which the destruction of the microbubble would be clearly distinguishable from motion induced signals.

In accordance with the principles of the present invention, a diagnostic ultrasound system is provided for detection of rupturing coated microbubble contrast agents. Following infusion of the contrast agent into the body an area of the body containing the coated microbubbles is insonified with ultrasonic energy of a sufficient energy to rupture microbubbles in the path of the ultrasonic waves. Acoustic energy emanating from the sites of microbubble destruction is received by an ultrasonic transducer and the resultant signals detected by amplitude detection of the received signal waveform. The echoes received from a subsequent ultrasonic transmission are detected in the same manner and the signals from the two reception periods are differentiated on a spatial basis. In the illustrated embodiment the signals of the second reception period are subtracted from those of the first reception period. This differentiation will, following post processing including thresholding, reveal the signals emanating from the microbubble destruction events to the exclusion of other signals. A useful application of detection of microbubble collapse is aberration correction, by which the event signals from separate channels of an ultrasonic beamformer are compared for coherent timing and the time delays of the beamformer channels adjusted to compensate for aberrations in the ultrasonic transmission medium.

In the drawings:

FIG. 3 illustrates aberration correction of an ultrasonic beamformer through detection of a microbubble destruction event; and FIG. 4 illustrates beamformer signals typical of the aberration correction arrangement of FIG. 3.

Figure 1:
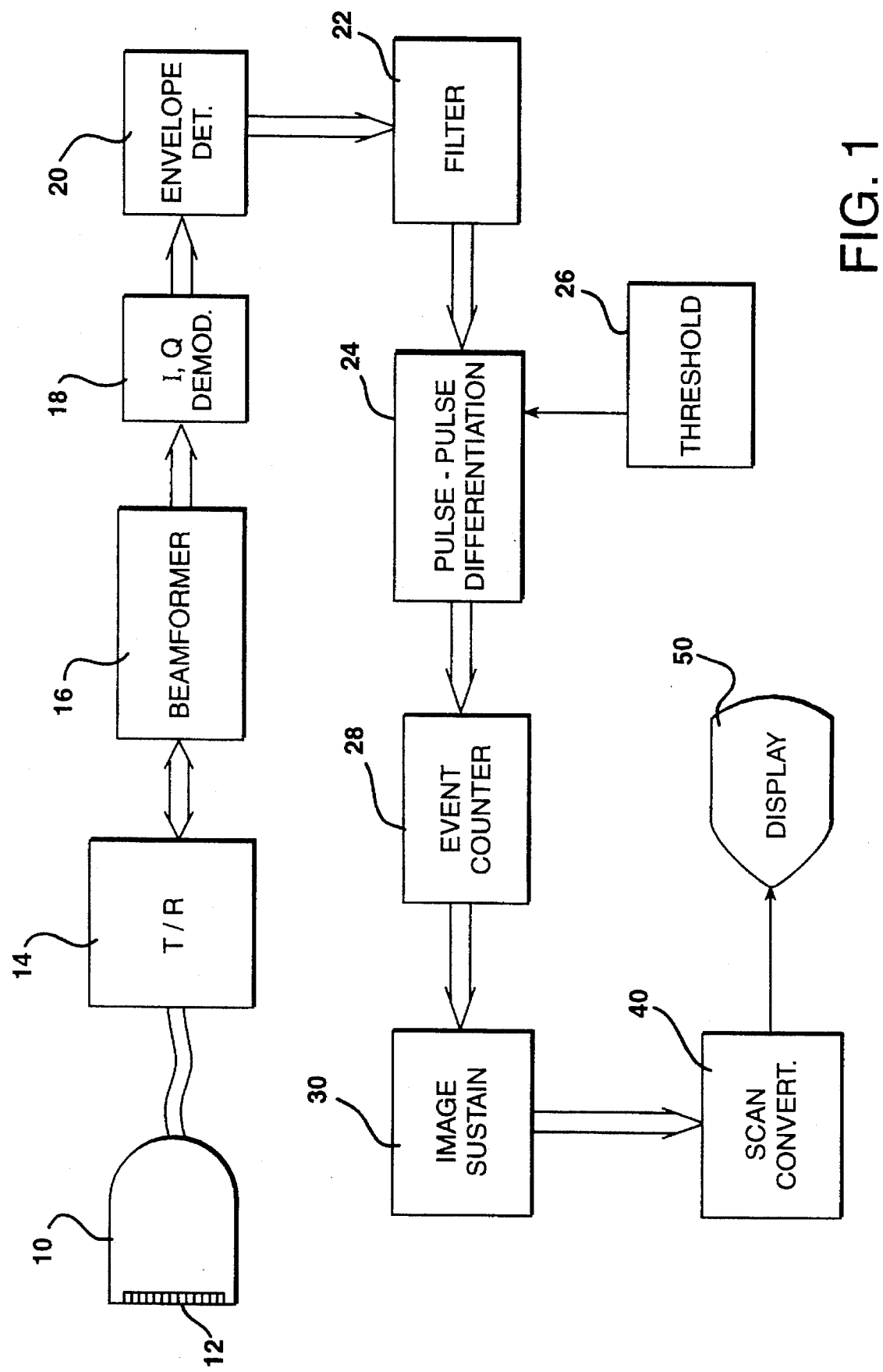
FIG. 1 is a block diagram of an ultrasonic diagnostic system constructed to detect the destruction of coated microbubbles in accordance with the principles of the present invention.

Referring first to FIG. 1, a block diagram of an ultrasonic diagnostic system constructed in accordance with the principles of the present invention is shown. An ultrasonic probe includes an array 12 of ultrasonic transducers which transmit and receive ultrasonic energy. During transmission an ultrasonic beamformer 16 controls the timing of actuation of the separate elements of the array 12 and activates the transducer pulsers of a transmitter/receiver 14 at appropriate times to pulse the transducer element so that a steered and focused ultrasonic beam is produced. During reception ultrasonic echoes received by the transducer elements are received by separate receivers of the transmitter/receiver 14 and coupled to separate channels of the beamformer 16, where the signals are appropriately delayed then combined to form a sequence of coherent echo signals over the depth of reception in the body of the patient.

The coherent echo signals are quadrature demodulated by an I,Q demodulator 18 which produces quadrature I and Q signal components. The demodulated signal components are then amplitude detected by an envelope detector 20. The detected signals are filtered by a filter 22 to remove noise and other extraneous signal components. A first such sequence of detected echo signals is stored for subsequent use by a pulse to pulse differentiation subsystem 24.

A second such sequence is received and detected from the same direction and in the same manner as the first sequence. When the transmitted pulses are of sufficient intensity to cause any coated microbubbles in the path of the ultrasonic beams to rupture, and the pulses are transmitted over the same path in relatively rapid succession, the first pulse will cause the coated microbubbles to rupture, sending acoustic waves back to the transducer array where the waves are received and processed by the system. When the second pulse is transmitted a relatively short time thereafter there will be no signals emanating from the same locations where microbubbles were ruptured by the first pulse. The second sequence of echo signals is then subtracted on a spatial basis from the signals of the first sequence by the pulse to pulse differentiation subsystem 24. Echoes returning from stationary tissue in the path of the two beams will be reproduced substantially similarly in the two sequences and will cancel through subtraction. But the signals received during the first sequence from microbubble destruction events will not be canceled by corresponding signals in the second sequence. The results of the subtraction process are compared against a threshold level supplied by a threshold circuit 26, which will eliminate minor variations of echoes received from tissue and flowing fluids in the two sequences, leaving only the signals returned from the microbubble destruction events.

The detected microbubble destruction events may be further processed and displayed in a variety of ways. One way is to display this information on the basis of the number of events that have occurred in a given region of the body in a period of time. In FIG. 1 the pulse to pulse differentiation subsystem 24 is followed by an event counter 28 which counts microbubble destruction events along each beam path in the region scanned and computes the frequency of such events. The occurrence of a significant number of events in a period of time is indicated by highlighting the corresponding region of an image of the body with image brightness or color. For example, the coated microbubble contrast agent can be injected into the blood stream of a patient and an area of the vascular system such as the heart can be monitored in this manner. As the contrast agent begins flowing into the heart the ultrasonic scanning will begin to induce microbubble destruction and the chambers of the heart into which the contrast agent is flowing will be highlighted in brightness or color. A compound image similar to that of color flow imaging can be formed, in which a structural image of the heart is overlaid with color which spatially depicts the frequency of microbubble destruction events in the imaged areas of the heart.

Another display alternative is to display each microbubble destruction event in the image as it occurs. But since these events are essentially instantaneous events, a real time display will be too transitory to be diagnostically meaningful. To account for this fact, an image sustain subsystem 30 is provided which causes each displayed event to be sustained in an image for a period of time. Even though a single event occurs in response to a single ultrasonic pulse, the detected event persists on the image display for a substantial period of time. A user controls the persistence period to range from tenths of a second to more than a second, as preferences dictate. The sustained event display can be modulated as increasing brightness or colors, and can be overlaid with a structural image as discussed above. The event counter 28 and the image sustain subsystem 30 can be employed together for a sustained image display based on the frequency of events, or the two can be employed alternatively and separately. In either case the spatially defined event information is coupled to a scan converter 40 where it is arranged in a desired image format and overlaid with a structural (B-mode) image if desired, and the resulting image is displayed on a display 50.

Figure 2A:
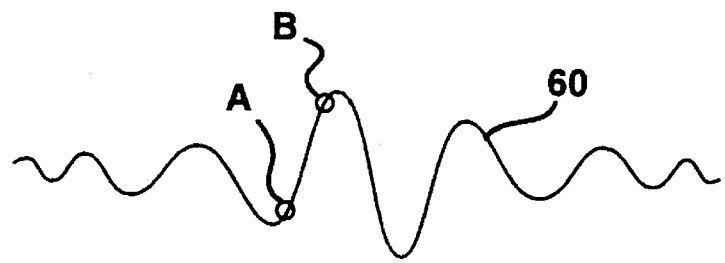
FIGS. 2a, 2b and 2c are waveforms illustrating the advantage of amplitude detection of microbubble destruction events.
Figure 2B:
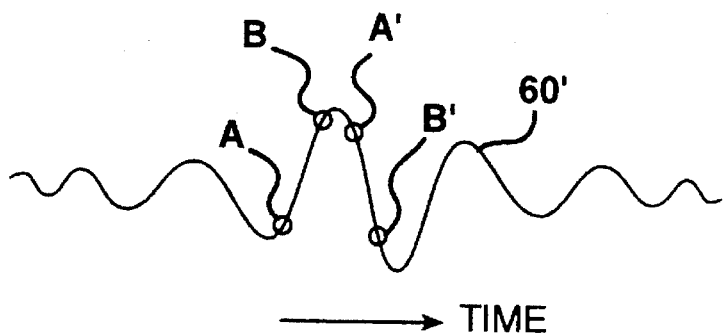
Figure 2C:
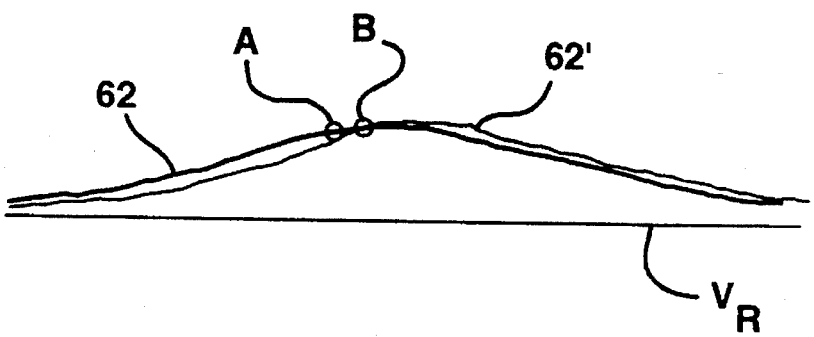

The reason why amplitude detection of microbubble destruction events is to be preferred over Doppler signal processing may be understood by referring to FIGS. 2a, 2b and 2c. FIG. 2a shows a waveform 60 depicting a received Doppler waveform resulting from the motion of tissue inside the body, such as motion of the heart wall. Points A and B on the waveform indicate two points in time at which the phase of the waveform is sampled. FIG. 2b illustrates a second received Doppler waveform 60' which is sampled at the same two points in sampling time alignment with points A and B. This time alignment means that the second waveform 60' is not sampled at points A and B shown on the waveform, but at points A' and B'. It is seen that there is a considerable phase difference of the Doppler signal between the A samples and the B samples of the two waveforms.

But when the envelope of the Doppler waveforms 60 and 60' are detected the envelopes 62 and 62' will appear as shown in FIG. 2c. In this figure the waveform envelopes are shown in comparison to a reference level, $V_R$. FIG. 2c shows that full wave envelope detection of the waveforms 60 and 60' will cause the sample values at points A and B to exhibit little amplitude difference, and that there is little difference between the amplitudes of envelopes 62 and 62' at the A and B sampling times. Hence the sharp waveform phase differences at points A and B will not be identified as a microbubble destruction events when amplitude detection is employed to detect such events. The difference required for detection of a microbubble destruction event is a substantial amplitude difference between the envelope levels at the respective sampling times. Thus, by detecting microbubble destruction events through a phase insensitive technique such as envelope detection, the events can be detected unambiguously.

The acoustic pulse resulting from a microbubble destruction event can be used adaptively by the diagnostic system to adjust the beamformer timing for aberrations produced by the medium through which the ultrasonic waves travel. Referring to FIG. 3, the transducer array 12 of the probe 10 is shown transmitting an ultrasonic beam into the body of a patient. The profile BP of the ultrasonic beam is indicted by the dashed lines emanating from the transducer array 12. As the ultrasonic wave components emitted by the elements of the array travel through the body of the patient they travel through different layers 92, 94 of skin, muscle, fat, and other types of tissue. Echoes returning from tissue interfaces return to the transducer array through the same layers. While it is conventionally assumed that ultrasonic waves will travel at a predetermined, fixed velocity (e.g., 1540 m/sec.) through tissue, this is not always true in practice; the velocity of the ultrasonic waves can vary slightly depending upon the tissue through which it is traveling. As a result, the time required for a pulse to travel out from a transducer element and back as an echo over the same path can vary from that which is theoretically predicted. Moreover, these times of travel can vary from one transducer element to another along the aperture 13 of the array as different elements along the aperture are opposed by different types of tissue of different thicknesses. As a consequence the time delays of the beamformer, chosen to equalize the times of travel of each signal component but predicated upon a theoretical, constant ultrasonic velocity, will be slightly incorrect. This will cause the combined output signal from the different channels to be slightly out of focus by reason of the aberrations in the uniformity of the medium of the tissues of the body.

As indicated above, the aberration problem is compounded in a pulse echo ultrasound system by the fact that the outbound transmitted pulses encounter these aberrations, then the incoming acoustic echoes also encounter aberrations in the acoustic medium. The combination of the two means that the transmitted beam may not be perfectly focused, and the received echo components may also not be perfectly focused. The present inventors have determined that microbubble destruction events are a means for overcoming a major portion of these limitations. In accordance with the principles of the present invention, the event of a microbubble collapse is used as a point source of ultrasonic energy within the medium being imaged, the tissues of the body. Problems of aberration affected transmit focus are obviated by inducing this generation of point source acoustic energy. The acoustic energy emanating from the event of a microbubble destruction travels along the different acoustic paths leading to the different transducer elements of the array aperture 13, encountering different materials in each path. The received event signal components are coupled from the separate elements of the array 12 through separate channels of the transmitter/receiver 14 to separate channels of the beamformer 16. In FIG. 3, the delays of five of the channels of the beamformer are represented by DL1 through DL5, with the length of each representing the length of the delay in time of that particular channel. At the outputs of the delays the individual signals components from the elements of the transducer are combined by a summer 17 to produce a focused, coherent signal for subsequent signal processing.

To produce a perfectly focused signal the signal components from each echo must appear simultaneously at the outputs of all of the delays, with the delays compensating exactly for variations in the time required for each echo component to travel to a transducer element. But if the velocity of ultrasound through the body has varied due to aberration effects, some signal components may appear at the outputs of the delays earlier or later than others. FIG. 4 shows echo signal components 100–104 produced at the outputs of the five delays whose times of travel have been affected by aberration effects. If the delay times exactly compensated for variations in acoustic wave travel from element to element, the five signals would be in alignment with time $t_n$. But the example shows that the acoustic signal component delayed by channel delay DL4 has experienced a lower acoustic velocity than the others and has been delayed beyond time $t_n$. Also it is seen that the acoustic signal component delayed by channel delay DL3 has experienced a higher acoustic velocity than the others and has arrived at the output of delay DL3 prior to time $t_n$. The other three signal components 101, 102, and 104 are all seen to be properly in alignment at time $t_n$.

These delay inaccuracies can be detected and adjusted through induced microbubble destruction events. FIG. 3 shows a blood vessel 80 in which the blood stream has been infused with a coated microbubble contrast agent. The ultrasonic probe 10 images the blood vessel 80 and begins pulsing the blood flow with ultrasonic pulses sufficient to cause rupturing of the shell of a microbubble. The pulses are transmitted in beams defined by the beam profile BP. As the probe pulses the blood flow the ultrasound system continually processes received echoes as discussed above to detect microbubble destruction events. One such event is depicted in the blood vessel 80 as indicated by arrow 82. The rupturing of this microbubble will be an effective point source transmission of acoustic energy from the point in the vessel where the microbubble is located when it ruptures. The rupture of the microbubble will radiate acoustic energy back to the aperture 13 of the transducer array 12, where acoustic signal components of the event will be received by different transducer elements along the aperture at slightly differing times.

The echo components received by the transducer elements following each pulsing of the blood vessel are separately delayed and temporarily stored in an echo storage and compare module 110. The echo components are also combined by a summer 17 to form a coherent echo signal sequence along the direction of the transmitted beam and these echo signals are processed as shown in FIG. 1 for detection of microbubble destruction events. If no event is detected there is no further need for storage of the separate signal components by the module 110, which is readied for storage of echo components from the next pulse sequence.

When a microbubble destruction event 82 is detected the location of the event along the beam direction by the processing system of FIG. 1 is supplied to the echo storage and compare module 110, informing the module of the time $t_n$ where the event should be located in time. The module 110 then begins to compare the event signal components 100–104 of the separate delays to see if the signal components are all in alignment at time $t_n$. When the comparison shows that signal component 100 has experienced a greater delay than the others, a command is sent to a delay adjust circuit 112, which adjusts the delay time of delay DL4 to a slightly shorter delay time to bring components processed by that channel back into coincidence with the others. Similarly when the comparison shows that a signal component 103 needs a greater delay to bring it into coincidence with the others at time $t_n$, a command is sent to the delay adjust circuit 112 which causes a compensating increase in the delay time of delay DL3. With the delays so adjusted for optimal focus, a sharper image will be acquired from the image field.

These adjustments in the delay timing for signal reception are equally applicable to the transmission timing. Effects in the image field which vary the velocity of ultrasonic echoes traveling back to the transducer will equally affect outbound waves transmitted by the transducer. Hence the timing adjustments made to the third and fourth receive channels will also be made to correspondingly advance or retard the timing of transmit pulse production on these channels, enabling focused insonification of all transmitted pulse components in the transmit focal region.

It will be appreciated that the tissue materials which are the source of the aberration inaccuracies will change whenever the position of the probe 10 is changed, causing the acoustic signal components to pass through different layers and combinations of tissues and substances. Accordingly the sequence of event detection, timing comparison and delay adjustment is continuously performed on a periodic basis, continually trimming the delays for optimal focus at each probe position. Aberration correction will thus be effective for so long as the coated microbubbles of the contrast agent are present in the image field.

What is claimed is:

1. A method for detecting the presence of a coated microbubble contrast agent in the body of a patient through ultrasonic interrogation comprising the steps of:

transmitting ultrasonic pulses into the body of a patient at an energy level sufficient to cause the destruction of coated microbubbles in the body;

receiving the signals returned following each pulse transmission;

detecting the signals received through phase insensitive detection;

differentiating the detected signals received following two pulse transmissions on a spatial basis; and identifying signal differentiations which exceed a predetermined threshold as resulting from microbubble destruction events.

2. The method of claim 1, wherein the step of detecting comprises detecting the signals received through envelope detection.

3. The method of claim 2, wherein the step of differentiating comprises subtracting the signals received following a later pulse transmission from the signals received following an earlier pulse transmission on a spatial basis, whereby the signals of each subtracted pair are received from the same location in the field being interrogated.

4. The method of claim 3, further comprising the steps of:

counting the number of identified microbubble destruction events; and displaying an image which depicts the number of events counted.

5. The method of claim 4, wherein the step of displaying comprises the step of displaying an ultrasonic image of the interior of the body of the patient and depicting the number of events counted in correspondence with said ultrasonic image.

6. The method of claim 5, wherein the step of displaying comprises the step of displaying an ultrasonic image of the interior of the body of the patient and depicting the number of events counted in color on said ultrasonic image.

7. The method of claim 3, further comprising the steps of:

displaying an ultrasonic image of the interior of the body of the patient; and displaying identified microbubble destruction events in correspondence with said ultrasonic image.

8. The method of claim 7, wherein the step of displaying identified microbubble destruction events comprises displaying said events in said ultrasonic image in spatial correspondence therewith, and displaying said events for times longer than the actual time span of an event occurrence.

9. The method of claim 1, wherein the step of receiving comprises receiving the signals returned following each pulse transmission with the elements of a multielement transducer array and separately delaying the signal component received by each transducer element; and further comprising the step of checking the coincidence of said delayed signal components in response to the identification of a microbubble destruction event.

10. An ultrasonic diagnostic system for detecting the presence of a coated microbubble contrast agent in the body of a patient through ultrasonic interrogation comprising:

an ultrasonic transducer which transmits ultrasonic pulses into the body of a patient at an energy level sufficient to cause the destruction of coated microbubbles in the body, and which receives the acoustic signals returned following each pulse transmission and converts them to electrical echo signals;

a phase insensitive detector for detecting said echo signals;

a differentiator which differentiates on a spatial basis the detected echo signals resulting from two pulse transmissions; and means for identifying differentiated echo signals which exceed a threshold as resulting from microbubble destruction events.

11. The ultrasonic diagnostic system of claim 10, wherein said phase insensitive detector comprises an envelope detector.

12. The ultrasonic diagnostic system of claim 10, wherein said differentiator comprises a subtractor which subtracts a sequence of echo signals following a later pulse transmission from a sequence of echo signals following an earlier pulse transmission in correspondence with the times of reception of echo signals of each sequence.

13. The ultrasonic diagnostic system of claim 10, further comprising:

an event counter for counting identified microbubble destruction events; and a display for displaying the count of said event counter.

14. The ultrasonic diagnostic system of claim 13, wherein said display comprises an image display for concurrently displaying an ultrasonic image of the interior of the body of a patient and locations in said image corresponding to counted microbubble destruction events.

15. The ultrasonic diagnostic system of claim 10, further comprising:

an image display for concurrently displaying an ultrasonic image of the interior of the body of a patient and locations in said image corresponding to spatial locations of microbubble destruction events; and further comprising:

means, coupled to said image display and responsive to the identification of a microbubble destruction event for displaying said event for a time greater than the duration of said event.

16. The ultrasonic diagnostic system of claim 10, wherein said ultrasonic transducer comprises a multielement transducer; and further comprising:

a beamformer, coupled to the elements of said transducer and to said detector, for controlling the timing of pulse transmission by said transducer elements and the timing of delays applied to said electrical echo signals; and an aberration correction subsystem, responsive to the identification of a microbubble destruction event, and coupled to said beamformer for adjusting the timing of said beamformer.

17. An ultrasonic diagnostic system which utilizes a coated microbubble contrast agent for aberration correction comprising:

an ultrasonic transducer array which transmits ultrasonic pulses into the body of a patient at an energy level sufficient to cause the destruction of coated microbubbles in the body, and which receives the acoustic signals returned following each pulse transmission and converts them to electrical echo signals;

a beamformer, coupled to said ultrasonic transducer array, for controlling the timing of pulse transmission by said transducer array and the timing of delays applied to said electrical echo signals; and a detector, coupled to said beamformer and responsive to said electrical echo signals, for detecting microbubble destruction events; and a beamformer timing check subsystem, coupled to said beamformer, for checking the timing of said beamformer in response to the detection of a microbubble destruction event.

18. The ultrasonic diagnostic system of claim 17, wherein said beamformer comprises a plurality of delay channels for applying adjustable delays to said electrical echo signals; and wherein said beamformer timing check subsystem includes means for adjusting said adjustable delays in response to the time coincidence of electrical echo signals of a microbubble destruction event which have been delayed by said beamformer delay channels.

* * * * *